United States Patent [19]

Cavalla et al.

[11] Patent Number: 4,950,681
[45] Date of Patent: Aug. 21, 1990

[54] KETONE DERIVATIVES

[75] Inventors: David J. Cavalla; William L. Mitchell, both of London, England

[73] Assignee: Glaxo Group Limited, London, England

[21] Appl. No.: 239,750

[22] Filed: Sep. 2, 1988

[30] Foreign Application Priority Data

Sep. 3, 1987 [GB] United Kingdom ............... 8720693

[51] Int. Cl.$^5$ ................... A61K 31/415; C07D 231/12
[52] U.S. Cl. .................................. 514/397; 514/212; 514/323; 540/603; 546/201; 548/336
[58] Field of Search .................... 548/336; 546/201; 540/603; 514/212, 323, 397

[56] References Cited

U.S. PATENT DOCUMENTS

| | | |
|---|---|---|
| 3,634,420 | 1/1972 | Littell et al. |
| 3,740,404 | 6/1973 | Littell et al. |
| 4,006,137 | 2/1977 | Haugwitz et al. |
| 4,619,941 | 10/1986 | Wright, Jr. et al. ............... 548/336 |
| 4,695,578 | 9/1987 | Coates et al. ...................... 548/336 |
| 4,725,615 | 2/1988 | Coates et al. ...................... 548/336 |
| 4,749,718 | 6/1983 | Coates et al. ...................... 548/336 |
| 4,808,581 | 2/1989 | Oxford et al. ................. 548/336 X |
| 4,814,344 | 3/1989 | Humbor et al. ..................... 548/336 |
| 4,822,881 | 4/1989 | Coates et al. ...................... 548/336 |
| 4,859,662 | 8/1989 | Coates et al. ...................... 548/336 |

FOREIGN PATENT DOCUMENTS

| | | |
|---|---|---|
| 155828A | 3/1984 | European Pat. Off. |
| 156603A | 3/1984 | European Pat. Off. |
| 164860A | 5/1984 | European Pat. Off. |
| 175551A | 9/1984 | European Pat. Off. |
| 131302A | 1/1985 | European Pat. Off. |

OTHER PUBLICATIONS

R. Littell et al, *J. Med. Chem.*, 1972, 15(8), 875–876 (1972).

*Primary Examiner*—Mary C. Lee
*Assistant Examiner*—Jacqueline Haley
*Attorney, Agent, or Firm*—Bacon & Thomas

[57] ABSTRACT

The invention relates to ketones of the general formula (I):

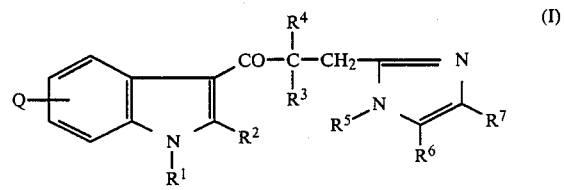

wherein
$R^1$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkylC$_{1-4}$alkyl, phenyl, phenylC$_{1-3}$alkyl, —CO$_2$R$^8$, —COR$^8$, —CONR$^8$R$^9$ or —SO$_2$R$^8$ (wherein $R^8$ and $R^9$, which may be the same or different, each represents a hydrogen atom, a $C_{1-6}$alkyl or $C_{3-7}$cycloalkyl group, or a phenyl or phenylC$_{1-4}$alkyl group, in which the phenyl group is optionally substituted by one or more $C_{1-4}$-alkyl, $C_{1-4}$alkoxy or hydroxy groups or halogen atoms, with the proviso that $R^8$ does not represent a hydrogen atom when $R^1$ represents a group —CO$_2$R$^8$ or —SO$_2$R$^8$);
$R^2$ represents a hydrogen atom or a $C_{1-6}$alkyl, $C_{3-6}$alkenyl, $C_{3-7}$cycloalkyl, phenyl or phenylC$_{1-3}$alkyl group;
$R^3$ and $R^4$, which may be the same or different, each represents a hydrogen atom or a $C_{1-6}$alkyl group; or $R^2$ and $R^3$ may together represent an alkylene chain —(CH$_2$)$_n$—, where n represents 1, 2 or 3;
one of the groups represented by $R^5$, $R^6$ and $R^7$ is a hydrogen atom or a $C_{1-6}$alkyl, $C_{3-7}$cycloalkyl, $C_{3-6}$alkenyl, phenyl or phenylC$_{1-3}$alkyl group, and each of the other two groups, which may be the same or different, represents a hydrogen atom or a $C_{1-6}$alkyl group;
Q represents a hydrogen atom or a halogen atom or a hydroxy, $C_{1-4}$alkoxy, phenylC$_{1-3}$alkoxy or $C_{1-6}$alkyl group or a group —NR$^{10}$R$^{11}$ or —CONR$^{10}$R$^{11}$ (wherein $R^{10}$ and $R^{11}$, which may be the same or different, each represents a hydrogen atom or a $C_{1-4}$alkyl or $C_{3-4}$alkenyl group, or together with the nitrogen atom to which they are attached form a saturated 5 to 7 membered ring);
and physiologically acceptable salts and solvates thereof.

The compounds are potent and selective antagonists of the effect of 5-HT and 5-HT$_3$ receptors and are useful, for example, in the treatment of psychotic disorders, anxiety, and nausea and vomiting.

10 Claims, No Drawings

KETONE DERIVATIVES

This invention relates to ketone derivatives, to processes for their preparation, to pharmaceutical compositions containing them and to their medical use.

In particular the invention relates to compounds which are potent and selective antagonists of 5-hydroxytryptamine (5-HT) at 5-HT receptors of the type located on terminals of primary afferent nerves. Receptors of this type are now designated as $5\text{-}HT_3$ receptors and are also present in the central nervous system. 5-HT occurs widely in the neuronal pathways in the central nervous system and disturbance of these 5-HT containing pathways is known to alter behavioural syndromes such as mood, psychomotor activity, appetite and memory.

Compounds having antagonist activity at $5\text{-}HT_3$ receptors have been described previously.

Thus for example published UK Patent Specification No. 2153821A and published European Patent Specifications Nos. 191562, 219193 and 210840 disclose 3-imidazolylmethyltetrahydrocarbazolones which may be represented by the general formula:

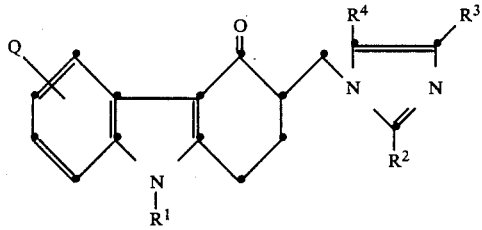

wherein
R$^1$ represents a hydrogen atom or a group selected from $C_{1-10}$ alkyl, $C_{3-6}$ alkenyl, $C_{3-10}$ alkynyl, $C_{3-7}$ cycloalkyl, $C_{3-7}$ cycloalkyl$C_{1-4}$ alkyl, phenyl or phenyl $C_{1-3}$ alkyl, and in the case where Q represents a hydrogen atom, R$^1$ may also represent —$CO_2R^5$, —$COR^5$, —$CONR^5R^6$ or —$SO_2R^5$ (wherein R$^5$ and R$^6$, which may be the same or different, each represents a hydrogen atom, a $C_{1-6}$ alkyl or $C_{3-7}$ cycloalkyl group, or a phenyl or phenyl $C_{1-4}$ alkyl group, in which the phenyl group is optionally substituted by one or more $C_{1-4}$ alkyl, $C_{1-4}$ alkoxy or hydroxy groups or halogen atoms, with the proviso that R$^5$ does not represent a hydrogen atom when R$^1$ represents a group —$CO_2R^5$ or —$SO_2R^5$);
one of the groups represented by R$^2$, R$^3$ and R$^4$ is a hydrogen atom or a $C_{1-6}$ alkyl, $C_{3-7}$ cycloalkyl, $C_{2-6}$ alkenyl, or phenyl $C_{1-3}$ alkyl group, and each of the other two groups, which may be the same or different, represents a hydrogen atom or a $C_{1-6}$ alkyl group; $C_{1-4}$ alkoxy, phenyl$C_{1-3}$ alkoxy or $C_{1-6}$ alkyl group or a group —NR'R$^8$ or —CONR$^7$R$^8$ (wherein R$^7$ and R$^8$, which may be the same or different, each represents a hydrogen atom or a $C_{1-4}$ alkyl or $C_{3-4}$ alkenyl group, or together with the nitrogen atom to which they are attached form a saturated 5 to 7 membered ring);
and physiologically acceptable salts and solvates thereof.

We have now found a novel group of compounds which differ in structure from those described previously, and which are potent antagonists of the effect of 5-HT at $5\text{-}HT_3$ receptors.

Thus, in one aspect the present invention provides a ketone of the general formula (I):

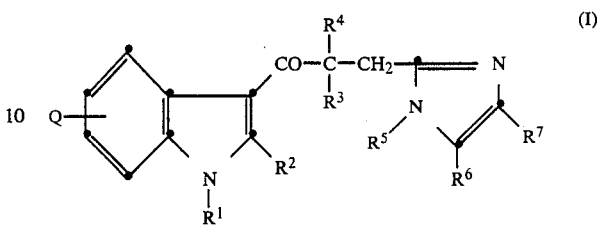

wherein
R$^1$ represents a hydrogen atom or a group selected from $C_{1-6}$ alkyl, $C_{3-6}$ alkenyl, $C_{3-10}$ alkynyl, $C_{3-7}$ cycloalkyl, $C_{3-7}$ cycloalkyl$C_{1-4}$ alkyl, phenyl, phenyl$C_{1-3}$ alkyl, —$CO_2R^8$, —$CO_2R^8$, —$COR^8$, —$CONR^8R^9$ or —$SO_2R^8$ (wherein R$^8$ and R$^9$, which may be the same or different, each represents a hydrogen atom, a $C_{1-6}$ alkyl or $C_{3-7}$ cycloalkyl group, or a phenyl or phenyl$C_{1-6}$ alkyl or $C_{3-7}$ cycloalkyl group, or a phenyl or phenyl$C_{1-4}$ alkyl group, in which the phenyl group is optionally substituted by one or more $C_{1-4}$ alkyl, $C_{1-4}$ alkoxy or hydroxy groups or halogen atoms, with the proviso that R$^8$ does not represent a hydrogen atom when R$^1$ represents a group —$CO_2R^8$ or —$SO_2R^8$);
R$^2$ represents a hydrogen atom or a $C_{1-6}$ alkyl, $C_{3-6}$ alkenyl, $C_{3-7}$ cycloalkyl, phenyl or phenyl$C_{1-3}$ alkyl group;
R$^3$ R$^4$, which may be the same or different, each represents a hydrogen atom or a $C_{1-6}$ alkyl group; or
R$^2$ and R$^3$ may together represent an alkylene chain —$(CH_2)_n$—, where n represents 1, 2 or 3;
one of the groups represented by R$^5$, R$^6$ and R$^7$ is a hydrogen atom or a $C_{1-6}$ alkyl, $C_{3-7}$ cycloalkyl, $C_{3-6}$ alkenyl, phenyl or phenyl$C_{1-3}$ alkyl group, and each of the other two groups, which may be the same or different, represents a hydrogen atom or a $C_{1-6}$ alkyl group;
Q represents a hydrogen atom or a halogen atom or a hydroxy, $C_{1-4}$ alkoxy, phenyl$C_{1-3}$ alkoxy or $C_{1-6}$ alkyl group or a group —NR$^{10}$R$^{11}$ or —CONR$^{10}$R$^{11}$ (wherein R$^{10}$ and R$^{11}$, which may be the same or different, each represents a hydrogen atom or a $C_{1-4}$ alkyl or $C_{3-4}$ alkenyl group, or together with the nitrogen atom to which they are attached form a saturated 5 to 7 membered ring);
and physiologically acceptable salts and solvates thereof.

Suitable physiologically acceptable salts of the compounds of general formula (I) include acid addition salts formed with organic or inorganic acids for example, hydrochlorides, hydrobromides, sulphates, alkyl sulphonates (e.g. methanesulphonates or p-toluenesulphonates), phosphates, citrates, succinates, tartrates, acetates, fumarates and maleates. The solvates may, for example, be hydrates.

All optical isomers of compounds of general formula (I) and their mixtures including the racemic mixtures thereof, and all the geometric isomers of compounds of formula (I), are embraced by the invention.

Referring to the general formula (I), the alkyl groups represented by $R^1$, $R^2$, $R^3$, $R^4$, $R^5$, $R^6$, $R^7$, $R^8$, $R^9$, $R^{10}$, $R^{11}$ and Q may be straight chain or branched chain alkyl groups, for example, methyl, ethyl, propyl, prop-2-yl, butyl, but-2-yl or 2-methylprop-2-yl, and, in the case of $R^1$–$R^9$ and Q, pentyl, pent-3-yl or hexyl. An alkenyl group may be, for example, a propenyl or butenyl group. An alkynyl group may be, for example, a prop-2-ynyl or oct-2-ynyl group.

When $R^1$ or $R^5$ represents a $C_{3-6}$ alkenyl group or $R^1$ represents a $C_{3-10}$ alkynyl group, or $R^{10}$ or $R^{11}$ represents a $C_{3-4}$ alkenyl group, the double or triple bond may not be adjacent to the nitrogen atom.

A phenyl$C_{1-3}$ alkyl group (as such or as part of a phenyl$C_{1-3}$ alkoxy group) may be, for example, a benzyl, phenethyl or 3-phenypropyl group. A cycloalkyl group (as such or as part of a cycloalkylalkyl group) may be, for example, a cyclopropyl, cyclobutyl, cyclopentyl, cyclohexyl or cycloheptyl group. A $C_{1-4}$ alkoxy group may be, for example, a methoxy group. A halogen atom may be, for example, a fluorine, chlorine or bromine atom.

The substituent Q may be at any position in the benzenoid ring.

A preferred class of compounds of formula (I) is that in which Q represents a hydrogen atom, a halogen (e.g. fluorine) atom, or a hydroxy, $C_{1-3}$ alkoxy (e.g. methoxy) or $C_{1-3}$ alkyl (e.g. methyl) group. Most preferably Q represents a hydrogen atom.

Another preferred class of compounds of formula (I) is that in which $R^1$ represents a hydrogen atom or a $C_{1-6}$ alkyl (e.g. methyl), $C_{3-4}$ alkenyl (e.g. prop-2-enyl), $C_{3-4}$ alkynyl (e.g. prop-2-ynyl), $C_{5-6}$ cycloalkyl (e.g. cyclopentyl), $C_{5-6}$ cycloalkylmethyl (e.g. cyclopentylmethyl), phenyl$C_{1-2}$alkyl (e.g. benzyl) or N,N-diC$_{1-3}$ alkylcarboxamido (e.g. N,N-dimethylcarboxamido) group. A particularly preferred class of compounds of formula (I) is that in which $R^1$ represents a hydrogen atom or, more preferably, a $C_{1-3}$ alkyl (e.g. methyl) group.

Another preferred class of compounds of formula (I) is that in which $R^2$ represents a $C_{1-6}$ alkyl (e.g. methyl) group or, more preferably, a hydrogen atom.

A further preferred class of compounds of formula (I) is that in which $R^2$ and $R^3$ together represent —(CH$_2$)$_2$—.

A further preferred class of compounds of formula (I) is that in which $R^3$ and $R^4$ each independently represents a hydrogen atom.

Another preferred class of compounds of formula (I) is that in which $R^5$, $R^6$ and $R^7$ each independently represents a hydrogen atom or a $C_{1-3}$ alkyl (e.g. methyl) group. Most preferably each of $R^5$, $R^6$ and $R^7$ represents a hydrogen atom.

A particularly preferred group of compounds of formula (I) is that in which Q represents a hydrogen atom; $R^1$ represents a hydrogen atom or, more preferably a $C_{1-3}$ alkyl (e.g. methyl) group; $R^2$ and $R^3$ each represent a hydrogen atom or together represent —(CH$_2$)$_2$—; $R^4$ represents a hydrogen atom; $R^5$, $R^6$ and $R^7$ each independently represents a hydrogen atom or a $C_{1-3}$ alkyl (e.g. methyl) group, more preferably a hydrogen atom.

Preferred compounds according to the invention are 1,2,3,9-tetrahydro-3-[(1H-imidazol-2-yl)methyl)]-9-methyl-4H-carbazolone and 3-1 -(1H-imidazol-2-yl)-1-(1-methyl-1H-indol-3-yl)-1-propanone, and their physiologically acceptable salts and solvates.

The potent and selective antagonism of 5-HT at 5-HT$_3$ receptors by compounds of the invention has been demonstrated by their ability to inhibit the 5-HT-induced depolarisation of the rat isolated vagus nerve preparation.

Compounds of formula (I), which antagonize the effect of 5-HT at 5-HT$_3$ receptors, are useful in the treatment of conditions such as psychotic disorders (e.g. schizophrenia and mania); anxiety; and nausea and vomiting, particularly that associated with cancer chemotherapy and radiotherapy. Compounds of formula (I) are also useful in the treatment of gastric stasis; symptoms of gastrointestinal dysfunction such as occur with dyspepsia, peptic ulcer, reflux oesophagitis, flatulence and irritable bowel syndrome; migraine; and pain. Compounds of formula (I) may also be used in the treatment of dependency on drugs and substances of abuse, depression, and dementia and other cognitive disorders.

According to another aspect, the invention provides a method of treatment of a human or animal subject suffering from a psychotic disorder such as schizophrenia or mania; or from anxiety; nausea or vomiting, particularly that associated with cancer chemotherapy and radiotherapy; gastric stasis; symptoms of gastrointestinal dysfunction such as dyspepsia, reflux oesophagitis, peptic ulcer, flatulence and irritable bowel syndrome; migraine; pain; dependency on drugs or substances of abuse; depression; or dementia and other cognitive disorders, which comprises administering an effective amount of a compound of formula (I) or a physiologically acceptable salt or solvate thereof.

Accordingly, the invention also provides a pharmaceutical composition which comprises at least one compound selected from ketone derivatives of the general formula (I), their physiologically acceptable salts and solvates (e.g. hydrates), for use in human or veterinary medicine, and formulated for administration by any convenient route.

Such compositions may be formulated in conventional manner using one or more physiologically acceptable carriers and/or excipients.

Thus the compounds according to the invention may be formulated for oral, buccal, parenteral, rectal or transdermal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipients such as binding agents (e.g. pregelatinized maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of the invention may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

In addition to the formulations described previously, the compounds of the invention may also be formulated as depot preparations. Such long acting formulations may be administered by implantation (for example subcutaneously, transcutaneously or intramuscularly) or by intramuscular injection. Thus, for example, the compounds of the invention may be formulated with suitable polymeric or hydrophobic materials (for example as an emulsion in an acceptable oil) or ion exchange resins, or a sparingly soluble derivatives, for example, as a sparingly soluble salt.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

For intranasal administration, the compounds according to the invention may be formulated as solutions for administration via a suitable metered or unit dose device or alternatively as a powder mix with a suitable carrier for administration using a suitable delivery device.

The compounds of formula (I) may also be administered in combination with other therapeutic agents. Thus, for example, in the treatment of gastric stasis, symptoms of gastrointestinal dysfunction and nausea and vomiting, the compounds of formula (I) may be administered in combination with antisecretory agents such as histamine $H_2$-receptor antagonists (e.g. ranitidine, sufotidine or 1-methyl-5-[[3-[3-(1-piperidinylmethyl)phenoxy]propyl]amino]-1H-1,2,4-triazole-3-methanol) or $H^+K^+$ATPase inhibitors (e.g. omeprazole).

A proposed dose of the compounds of the invention for administration to man (of approximately 70 kg body weight) is 0.05 to 100 mg, preferably 0.1 to 50 mg, most preferably 0.5 to 20 mg of the active ingredient per unit dose (expressed as the weight of free base) which could be administered, for example, 1 to 4 times per day. The dose will depend on the route of administration and the condition being treated. It will be appreciated that it may be necessary to make routine variations to the dosage depending on the age and weight of the patient as well as the severity of the condition to be treated.

According to another aspect of the invention, compounds of general formula (I) and physiologically acceptable salts or solvates thereof may be prepared by the general methods outlined hereinafter. In the following description, the groups $R^1$ to $R^7$, n and Q are as defined for compounds of general formula (I) unless otherwise stated.

According to a first general process (A) a compound of general formula (I) wherein $R^4$ represents a hydrogen atom, may be prepared by hydrogenation of a compound of formula (II):

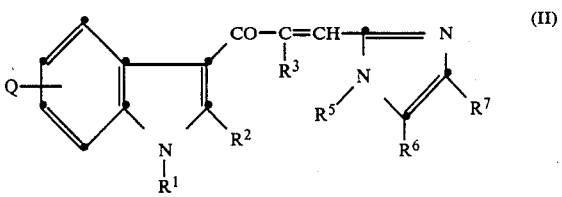

or a protected derivative thereof, followed where necessary by removal of any protecting groups.

Hydrogenation according to general process (A) may be effected using conventional procedures, for example using hydrogen in the presence of a noble metal catalyst (e.g. palladium, Raney nickel, platinum or rhodium). The catalyst may be supported on, for example, charcoal or alumina, or alternatively a homogeneous catalyst such as tris(triphenylphosphine)rhodium chloride may be used. The hydrogenation will generally be effected in a solvent such as an alcohol (e.g. methanol or ethanol), an ether (e.g. dioxan), or an ester (e.g. ethyl acetate), or in a mixture of an alcohol and either a hydrocarbon (e.g. toluene), a halogenated hydrocarbon (e.g. dichloromethane) or an ester (e.g. ethyl acetate), and at a temperature in the range $-20°$ to $+100°$ C., preferably $0°$ to $50°$ C.

Compounds of formula (II) are novel compounds and constitute a further aspect of the invention.

According to another general process (B), a compound of general formula (i) may be converted into another compound of formula (i) using conventional techniques. Such conventional techniques include hydrogenation, alkylation, acylation and acid-catalyzed cleavage using protection and deprotection where necessary.

Thus, according to one embodiment of the interconversion process (B), hydrogenation may be used to convert an alkenyl or an alkynyl substituent into an alkyl substituent, or an alkynyl into an alkenyl substituent, or a benzyloxy substituent into a hydroxyl group. Hydrogenation according to general process (B) may be effected using conventional procedures, for example as described above for general process (A).

Alkylation according to process (B) may be used to effect C—, N— or O— alkylation at any appropriate position in the molecule, and the term 'alkylation' also includes the introduction of other groups such as cycloalkyl, alkenyl or phenalkyl groups.

Thus, for example, a compound of formula (I) in which one or both of $R^3$ and $R^4$ represents a $C_{1-6}$alkyl group may be prepared by alkylating the corresponding compound of formula (I) in which one or both of $R^3$ and $R^4$ represent a hydrogen atom, or a compound in which $R^5$ represents a $C_{1-6}$alkyl, $C_{3-7}$cycloalkyl, $C_{3-6}$alkenyl or phenyl$C_{1-3}$alkyl group may be prepared by alkylating the corresponding compound of formula (I) in which $R^5$ represents a hydrogen atom.

The above alkylation reactions may be effected using conventional procedures, for example as described in published European Patent specification No. 242973. Thus the reactions may be effected using an appropriate alkylating agent of formula $R^{12}Z$ (where $R^{12}$ is the group to be introduced and Z is a leaving atom or group), preferably in the presence of a base.

According to another embodiment of general process (B), a compound of formula (I) wherein $R^1$ represents $-CO_2R^8$, $-COR^8$, $-CONR^8R^9$ or $-SO_2R^8$ may be prepared by acylating or sulphonylating as appropriate, a compound of formula (I) wherein $R^1$ represents a hydrogen atom. The acylation/sulphonylation reactions may be effected using an appropriate acylating-/sulphonylating agent according to conventional procedures, for example, as described in published European Patent Specification No. 210840.

According to a yet further embodiment of general process (B), a compound of formula (I) in which the group A contains a hydroxyl substituent may be prepared from the corresponding compound of formula (I) in which the group A is substituted by a $C_{1-4}$alkoxy or benzyloxy group, by acid-catalyzed cleavage. The reaction may be effected using a Lewis acid such as boron tribomide or aluminum trichloride, in a solvent such as a halogenated hydrocarbon (e.g. dichloromethane). The reaction temperature may conveniently be in the range $-80°$ to $+100°$ C.

It should be appreciated that in the above transformations it may be necessary or desirable to protect any sensitive groups in the molecule of the compound in question to avoid undesirable side reactions. For example, it may be necessary to protect the keto group, for example, as a ketal or a thioketal. It may also be necessary to protect any of the carbazolone, indole or imidazole nitrogen atoms, for example with an arylmethyl (e.g. benzyl or trityl), alkyl (e.g. t-butyl), alkoxymethyl (e.g. methoxymethyl), acyl (e.g. benzyloxycarbonyl) or a sulphonyl (e.g. N,N-dimethylaminosulphonyl or p-toluenesulphonyl) group. When Q represents a hydroxyl group it may be necessary to protect the hydroxyl group, for example with an arylmethyl (e.g. benzyl or trityl) group.

Thus according to another general process (C), a compound of general formula (I) may be prepared by the removal of any protecting groups from a protected form of a compound of formula (I). Deprotection may be effected using conventional techniques such as those described in 'Protective Groups in Organic Synthesis' by T. W. Greene (John Wiley and Sons, 1981).

For example a ketal such as an alkyleneketal group may be removed by treatment with a mineral acid such as hydrochloric acid. A thioketal group may be cleaved by treatment with a mercuric salt, (e.g. mercuric chloride), in a suitable solvent, such as ethanol. An arylmethyl N-protecting group may be cleaved by hydrogenolysis in the presence of a catalyst (e.g. palladium on charcoal) and a trityl group may also be cleaved by acid hydrolysis (e.g. using dilute hydrochloric or acetic acid). An alkoxyalkyl group may be removed using a mineral acid (e.g. dilute hydrochloric acid). An acyl group may be removed by hydrolysis under acidic or basic conditions (e.g. using hydrogen bromide or sodium hydroxide). A sulphonyl group may be removed by alkaline hydrolysis. An arylmethyl OH-protecting group may be cleaved under acidic conditions (e.g. with dilute acetic acid, hydrobromic acid or boron tribomide) or by hydrogenolysis in the presence of a catalyst (e.g. palladium on charcoal).

Compounds of formula (II) in which $R^2$ and $R^3$ together represent $-(CH_2)_n-$ may be prepared by condensing a compound of formula (III):

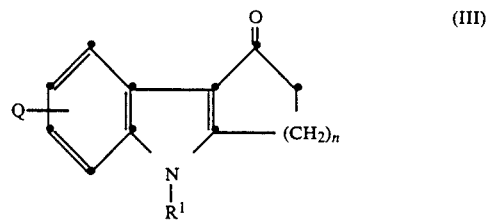

or a protected derivative thereof, with a compound of formula (IV):

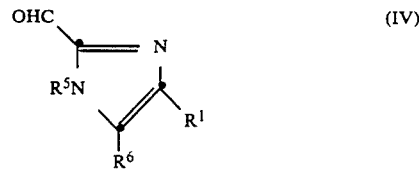

or a protected derivative thereof, in the presence of a base such as an alkali metal amide (e.g. lithium diisopropylamide) in an inert solvent such as an ether (e.g. tetrahydrofuran), followed by dehydration of the intermediate carbinol, and removal of any protecting groups where necessary.

The dehydration process may be effected using conventional methods, for example by using an organic or mineral acid (e.g. p-toluenesulphonic, methanesulphonic, trifluoroacetic or hydrochloric acid) in a suitable solvent such as an ether (e.g. tetrahydrofuran), an alcohol (e.g. methanol), or glacial acetic acid, at a temperature in the range of 0° to 100° C.

Compounds of formula (II) in which $R^3$ represents a hydrogen atom or a $C_{1-6}$alkyl group may be prepared, for example, by condensing a compound of formula (V):

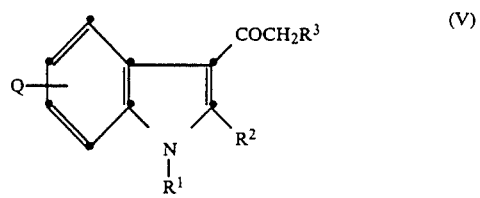

or a protected derivative thereof, with a compound of formula (IV) or a protected derivative thereof, in the presence of a base such as an alkali metal hydroxide or alkoxide, followed where necessary by removal of any protecting groups. The reaction may conveniently be effected using an alkali metal hydroxide (e.g. sodium or potassium hydroxide) in an alcohol (e.g. methanol or ethanol) or water, or mixtures thereof, or using an alkali metal alkoxide (e.g. sodium ethoxide or potassium t-butoxide) in the corresponding alcohol (e.g. ethanol or t-butanol) or in an inert solvent such as an ether (e.g. tetrahydrofuran), at a temperature of 0° to 100° C.

Compounds of formula (V) may be prepared, for example, by the method or methods analogous to that described in published European Patent Specification No. 242973.

Compounds of formula (III) may be prepared, for example, by the method or methods analogous to that described by H. Iida et al. in *J. Org. Chem.*, 1980, 45, 2938.

Compounds of formula (IV) are either known or may be prepared from known compounds by conventional procedures.

Where it is desired to isolate a compound of the invention as a salt, for example a physiologically acceptable salt, this may be achieved by reacting the compound of formula (I) in the form of the free base with an appropriate acid, preferably with an equivalent amount, in a suitable solvent such as an alcohol (e.g. ethanol or methanol), a mixture of an alcohol and a halogenated hydrocarbon (e.g. methanol and chloroform), an ester (e.g. ethyl acetate) or an ether (e.g. tetrahydrofuran).

Physiologically acceptable salts may also be prepared from other salts, including other physiologically acceptable salts, of the compound of formula (I) using conventional methods.

Individual enantiomers of the compounds of the invention may be obtained by resolution of a mixture of enantiomers (e.g. a racemic mixture) using conventional means, such as an optically active resolving acid; see for example 'Stereochemistry of Carbon Compounds' by E. L. Eliel (McGraw Hill 1962) and 'Tables of Resolving Agents' by S. H. Wilen.

The methods described above for preparing the compounds of the invention may be used for the introduction of the desired groups at any stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product.

The invention is further illustrated by the following Examples. All temperatures are in 0° C. Thin layer chromatography (t.l.c.) was carried out on silica, and flash column chromatography (FCC) on silica (Merck 9385). Organic extracts were dried over magnesium sulphate. The following abbreviation is used: THF—tetrahydrofuran.

EXAMPLE 1

1,2,3,9-Tetrahydro-3-[(1H-imidazol-2-yl)methyl)]-9-methyl-4H-carbazolone maleate

Stage (i)

(E)-1,2,3,9-Tetrahydro-3-[(1H-imidazol-2-yl)methylene]-9-methyl-4H-carbazol-4-one Lithium diisopropylamide (3.7 ml of a 1.5 M solution in cyclohexane) was added to a stirred suspension of 1,2,3,9-tetrahydro-9-methyl-9-methyl-4H-carbazol-4-one (1.0 g) in dry THF (75 ml) at −50° under nitrogen. After 1 h, a solution of 1-(triphenylmethyl)-1H-imidizole-2-carboxaldehyde (1.86 g) in dry THF (20 ml) was added and the mixture was stirred for 2 h while warming to room temperature. It was then recooled to −70° and quenched with saturated ammonium chloride solution (5 ml). Acetic acid (40 ml) and water (30 ml) were added and the mixture was heated on a steam bath for 1h, cooled and partitioned between dichloromethane (2×150 ml; discarded) and hydrochloric acid (0.2N; 200 ml). The acidic layer was carefully basified with solid potassium carbonate and extracted with dichloromethane:methanol (9:1) (3×150 ml). These latter organic layers were dried and evaporated to leave a solid (1.2 g) which was mixed with acetic acid (50 ml) and p-toluenesulphonic acid (2.5 g) and heated at reflux under nitrogen for 2.5 h. The cooled solution was partitioned between sodium hydroxide (2N; 300 ml) and dichloromethane (3×100 ml). The combined, dried organic extracts were evaporated and the residual solid was triturated with dichloromethane:ether (1:5) (100 ml), to give the title compound (0.88 g), m.p. 236°–240° (decomp.).

Stage (ii)

1,2,3,9-Tetrahydro-3-[(1H-imidazol-2-yl)methyl)]-9-methyl-4H-carbazol-4-one maleate A suspension of (E)-1,2,3,9-tetrahydro-3-[(1Himidazol-2-yl)-methylene]-9-methyl-4H-carbazol-4-one (500 mg) in ethanol (75 ml) was hydrogenated at room temperature and atmospheric pressure over a stirred suspension of pre-reduced 10% palladium oxide on carbon (50% aqueous paste; 50 mg) in ethanol (20 ml) for 8 h. The mixture was filtered, evaporated in vacuo and the residual yellow solid (0.5 g) was recrystallized from ethanol (ca. 25 ml) to give the free base of the title compound (400 mg). This was dissolved in chloroform:methanol (3:1) (40 ml) and treated with a solution of maleic acid (166 mg) in methanol (1 ml). Concentration of the resulting solution to ca. 5 ml and dilution with dry ether (30 ml) afforded the title compound (506 mg) as crystals, m.p. 124°–129°.

Analysis, Found: C, 62.8; H, 5.4; N, 10.2; $C_{17}H_{17}N_3O.C_4H_4O_4.0.22\ H_2O$ requires C, 63.2; H, 5.4; N, 10.5%. Water Analysis Found: 0.996% w/w≡0.22 mol $H_2O$.

EXAMPLE 2

3-(1H-Imidazol-2-yl)-1-(1-methyl-1H-indol-3-yl)-1-propanone maleate

Stage (i)

1-(1-Methyl-1H-indol-3-yl)-3-[1-(triphenylmethyl)-1H-imidazol-2-yl]-2-propen-1-one A solution of potassium hydroxide (2.5 g) in water (15 ml) was added to a stirred suspension of 3-acetyl-1-methylindole (1.0 g) and 1-(triphenylmethyl)-1H-imidazole-2-carboxaldehyde (2.0 g) in ethanol (40 ml), and the mixture was stirred under nitrogen at 50° for 6 h. The cooled reaction mixture was partitioned between dichloromethane (2×150 ml) and saturated potassium carbonate (150 ml). The combined, dried organic extracts were evaporated in vacuo to leave a solid (ca. 3 g) which was dissolved in chloroform (20 ml) and purified by FCC eluting with ethyl acetate, to give the title compound (0.64 g) t.l.c. (ethyl acetate) Rf 0.14.

Stage (ii)

3-(1H-Imidazol-2-yl)-1-(1-methyl-1H-indol-3-yl)-1-propanone maleate

A solution of 1-(1-methyl-1H-indol-3-yl)-3-[1-(triphenylmethyl)-1H-imidazol-2-yl]-2-propen-1-one (447 mg) in ethanol (10 ml) and ethyl acetate (50 ml) was hydrogenated at room temperature and atmospheric pressure over a stirred suspension of pre-reduced 10% palladium oxide on carbon (50% aqueous paste; 47 mg) in ethanol (15 ml) for 18 h. The reaction mixture was filtered and evaporated in vacuo to leave a foam (427 mg) which was dissolved in a mixture of acetic acid (10 ml), THF (5 ml) and water (10 ml) and heated under nitrogen at reflux for 0.75 h. The cooled reaction mixture was partitioned between ethyl acetate (100 ml) and hydrochloric acid (0.4N; 3×75 ml). The combined acidic layers were basified with solid potassium carbonate and extracted with dichloromethane (3×75 ml). The combined, dried dichloromethane extracts were evaporated in vacuo to give a solid (0.23 g) which was dissolved in chloroform: methanol (1:1) (10 ml). A solution of maleic acid (105 mg) in methanol (0.4 ml) was added with stirring and concentration of the resulting solution in vacuo followed by dilution with ether (50 ml) afforded the title compound (0.27 g) as a solid. The solid (0.25 g) was dissolved in hot ethanol (5 ml) and hot ethyl acetate (15 ml) was added. On cooling, the title compound precipitated as a solid (0.15 g), m.p. 170°-174° (decomp.), t.l.c. (dichloromethane:ethanol:0.88 ammonia, 19:10:1) Rf 0.43.

The following examples illustrate pharmaceutical formulations according to the invention. The term "active ingredient" is used herein to represent a compound of formula (I).

TABLETS FOR ORAL ADMINISTRATION

Tablets may be prepared by the normal methods such as direct compression or wet granulation.

The tablets may be film coated with suitable film forming materials, such as hydroxypropyl methylcellulose, using standard techniques. Alternatively the tablets may be sugar coated.

| Direct Compression Tablet | mg/tablet |
|---|---|
| Active Ingredient | 10.00 |
| Calcium Hydrogen Phosphate BP* | 77.75 |
| Croscarmellose Sodium NF | 1.80 |
| Magnesium Stearate BP | 0.45 |
| Compression weight | 90.00 |

*of a grade suitable for direct compression.

The active ingredient is passed through a 60 mesh sieve, blended with the calcium hydrogen phosphate, croscarmellose sodium and magnesium stearate. The resultant mix is compressed into tablets using a Manesty F3 tablet machine fitted with 5.5 mm, flat bevelled edge punches.

Tablets of other strengths may be prepared by altering the ratio of active ingredient to excipients or the compression weight and using punches to suit.

INJECTION FOR INTRAVENOUS ADMINISTRATION

|  | mg/ml |
|---|---|
| Active Ingredient | 1.0 |
| Sodium Chloride BP | as required |
| Water for Injection BP to | 1.0 ml |

Sodium chloride may be added to adjust the tonicity of the solution and the pH may be adjusted, using acid or alkali, to that of optimum stability and/or facilitate solution of the active ingredient. Alternatively suitable buffer salts may be used.

The solution is prepared, clarified and filled into appropriate size ampoules sealed by fusion of the glass. The injection is sterilized by heating in an autoclave using one of the acceptable cycles. Alternatively the solution may be sterilized by filtration and filled into sterile ampoules under aseptic conditions. The solution may be packed under an inert atmosphere of nitrogen or other suitable gas.

We claim:

1. A compound of formula (I):

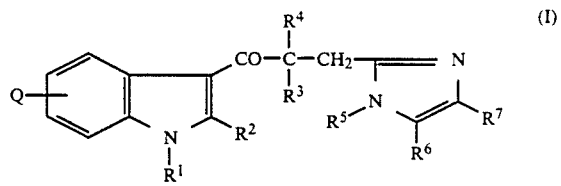

wherein
$R^1$ represents a hydrogen atom, $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl, phenyl, phenyl$C_{1-3}$alkyl, $-CO_2R^8$, $-COR^8$, $-CONR^8R^9$ or $-SO_2R^8$, and wherein $R^8$ and $R^9$, which may be the same or different, each represents a hydrogen atom, a $C_{1-6}$alkyl, $C_{3-7}$cycloalkyl group, a phenyl or phenyl$C_{1-4}$alkyl group, in which the phenyl group is optionally substituted by one or more $C_{1-4}$alkyl, $C_{1-4}$alkoxy or hydroxy groups or halogen atoms, with the proviso that $R^8$ does not represent a hydrogen atom when $R^1$ represents a group $-CO_2R^8$ or $-SO_2R^8$;

$R^2$ and $R^3$ together represent $-(CH_2)_n-$, wherein n is 1, 2 or 3;

$R^4$ represents a hydrogen atom or a $C_{1-6}$ alkyl group;

one of the groups represented by $R^5$, $R^6$ and $R^7$ is a hydrogen atom or a $C_{1-6}$alkyl, $C_{3-7}$cycloalkyl, $C_{3-6}$alkenyl, phenyl or phenyl$C_{1-3}$alkyl group, and each of the other two groups, which may be the same or different, represents a hydrogen atom or a $C_{1-6}$alkyl group;

Q represents a hydrogen atom or a halogen atom or a hydroxy, $C_{1-4}$alkoxy, phenyl$C_{1-3}$alkoxy or $C_{1-6}$alkyl group or a group $-NR^{10}R^{11}$ or $-CONR^{10}R^{11}$ (wherein $R^{10}$ and $R^{11}$, which may be the same or different, each represents a hydrogen atom or a $C_{1-4}$alkyl or $C_{3-4}$alkenyl group, or together with the nitrogen atom to which they are attached form a saturated 5 to 7 membered ring);

or a physiologically acceptable salt or solvate thereof.

2. A compound according to claim 1 in which Q represents a hydrogen atom, a halogen atom, or a hydroxy, $C_{1-3}$alkoxy or $C_{1-3}$alkyl group.

3. A compound according to claim 1 in which $R^1$ represents a hydrogen atom or a $C_{1-6}$alkyl, $C_{3-4}$alkenyl, $C_{3-4}$alkynyl, $C_{5-6}$cycloalkyl, $C_{5-6}$cycloalkylmethyl, phenyl$C_{1-2}$alkyl or N,N-di$C_{1-3}$alkylcarboxamido group.

4. A compound according to claim 1 in which $R^2$ and $R^3$ together represent $-(CH_2)_2-$.

5. A compound according to claim 1 in which $R^4$ represents a hydrogen atom.

6. A compound according to claim 1 which $R^5$, $R^6$ and $R^7$ each independently represent a hydrogen atom or a $C_{1-3}$alkyl group.

7. A compound selected from the group consisting of: 1,2,3,9-tetrahydro-3-[(1H-imidazol-2-yl)methyl)]-9-methyl-4H-carbazolone, or physiologically acceptable salts and solvates thereof.

8. A pharmaceutical composition for treating a condition mediated through 5-$HT_3$ receptors which comprises an effective amount to relieve said condition of a compound of formula (I) as defined in claim 1 or a physiologically acceptable salt or solvate thereof together with at least one physiologically acceptable carrier or excipient.

9. A method of treating a condition mediated through 5-$HT_3$ receptors which comprises administering to a patient an effective amount of a compound of formula (I) as defined in claim 1 or a physiologically acceptable salt or solvate thereof to relieve said condition.

10. A compound according to claim 4 in which Q represents a hydrogen atom; $R^1$ represents a hydrogen atom or a $C_{1-3}$ alkyl group, $R^4$ represents a hydrogen atom; and $R^5$, $R^6$ and $R^7$ each independently represents a hydrogen atom or a $C_{1-3}$ alkyl group.

* * * * *